United States Patent [19]

Zeikus et al.

[11] Patent Number: 4,647,538

[45] Date of Patent: Mar. 3, 1987

[54] THERMOSTABLE BETA-AMYLASE

[75] Inventors: Joseph G. Zeikus, Okemos, Mich.; Hyung-Hwan Hyun, Madison, Wis.

[73] Assignee: Michigan Biotechnology Institute, East Lansing, Mich.

[21] Appl. No.: 652,585

[22] Filed: Sep. 18, 1984

[51] Int. Cl.$^4$ .......... C12N 9/26; C12P 19/22; C12P 7/14; C12R 1/145

[52] U.S. Cl. .................. 435/201; 435/95; 435/162; 435/842

[58] Field of Search .......... 435/95, 201, 161, 162

[56] References Cited

U.S. PATENT DOCUMENTS 3,677,896 7/1972 Kurimoto et al. .......... 435/201 X
3,804,715 4/1974 Sugimoto et al. .......... 435/201 X
4,011,136 3/1977 Napier .......... 435/201 X

OTHER PUBLICATIONS

Srivastava et al., Acta Microbiologia Polonica vol. 33, No. 1, pp. 57–66, 1984.
H. H. Hyun et al., "Ultrastructure and Extreme Heat Resistance of Spores from Thermophilic Clostridium Species." J. Bact. 156: 1332–1337 (1983).
Bernard Schink et al., *Clostridium thermosulfurogenes* sp. Nov., a New Thermophile that Produces Elemental Sulphur from Thiosulphate," J. Gen. Microbiol. 129: 1149–1158 (1983).

*Primary Examiner*—Lionel M. Shapiro
*Attorney, Agent, or Firm*—Quarles & Brady

[57] ABSTRACT

A thermostable and thermoactive, extracellular β-amylase is produced by Clostridium thermosulfurogenes. Methods of producing the β-amylase and using it to convert starch to maltose are also disclosed.

3 Claims, 10 Drawing Figures

THERMOSTABLE BETA-AMYLASE

FIELD OF THE INVENTION

The present invention relates to enzymes. More particularly, it relates to a thermostable β-Amylase.

BACKGROUND OF THE INVENTION

The food and beverage industries principally employ the enzyme, β-amylase (EC 3.2.1.1.2), to convert starch into maltose solutions. β-Amylase hydrolyzes the α-1,4-glucosidic linkages in an exo-fashion from the non-reducing end of starch-type subtrates, and produces both maltose in the β-anomeric configuration and β-limit dextrins from starch. The β-amylase employed in most industrial applications is obtained from plants. Attempts have been made to obtain a more active, thermostable and extracellular enzyme from microorganisms. However, the known microbial β-amylases are not active or thermostable enough to substitute for the plant enzyme. Therefore, the plant β-amylases continue to be used for maltose production although they are expensive and relatively unstable.

Only a few enzymes of current industrial interest have been isolated and characterized from thermoanaerobes. The thermostable and active enzymes characterized to date from thermoanaerobes, include an endoglucanase of *Clostridium thermocellum*, an alcohol dehydrogenase of *Thermoanaerobium brockii* and *C. thermohydrosulfuricum* and a polygalacturonate hydrolyase of *C. thermosulfurogenes* (1,2). It would obviously be desirable to have a more thermostable β-amylase than those currently available.

BRIEF SUMMARY OF THE INVENTION

The primary objects of the present invention are to disclose a thermostable β-amylase and a method of producing that enzyme.

We have discovered that the organism *Clostridium thermosulfurogenes* produces a unique thermostable and thermoactive β-amylase. The enzyme is extracellular and has an optimum temperature for activity at 75° C. It is stable up to 70° C. in the absence of substrate and up to 80° C. in the presence of 5% starch. The optimum activity of the enzyme is at about pH 5.5 to about 6.0. The β-amylase of the present invention appears to be particularly suited for use in industrial applications.

The β-amylase is produced by culturing *C. thermosulfurogenes* anaerobically on a substrate of starch in a nutrient medium containing essential vitamins, minerals and growth factors until substantial enzymatic activity is detectable and then isolating the β-amylase. The β-amylase is produced extracellularly and therefore is easily separated from the cells and isolated in purified form substantially free of interfering enzymatic activity.

DESCRIPTION OF PREFERRED EMBODIMENT

Figure 1A:
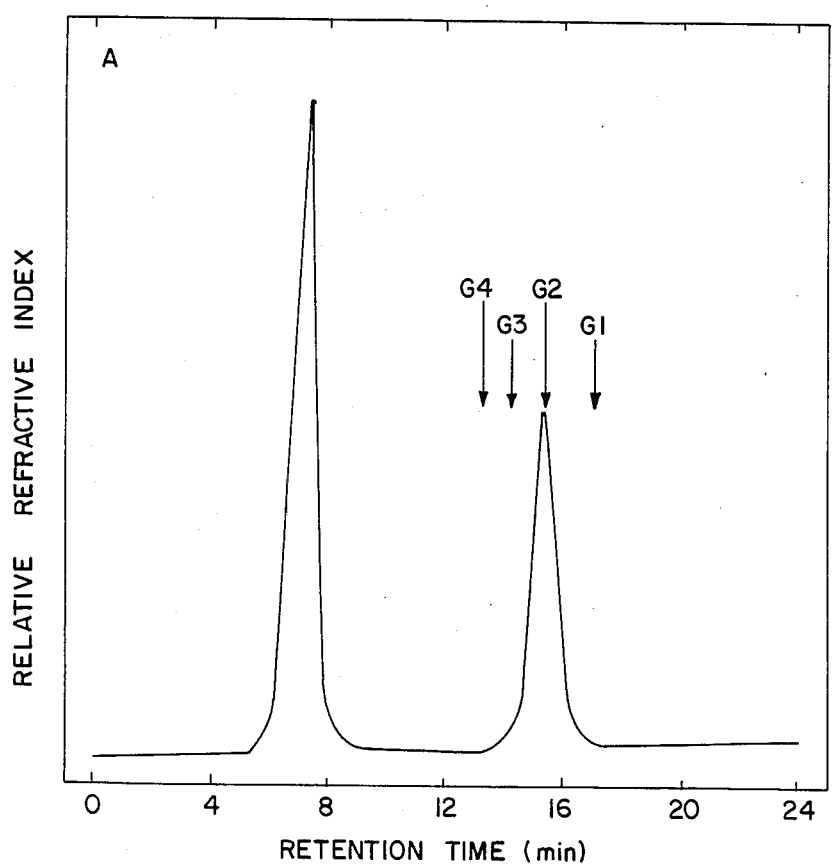
FIG. 1. Shows the starch hydrolysis by *C. thermosulfurogenes* extracellular amylase. 1% starch solution (20 ml) in 0.1 phosphate buffer, pH 6.0, (A) or in 0.1 M acetate buffer, pH 6.0 (B) was incubated with 12 units of enzyme at 65° C.
  A. Shows HPLC analysis of starch hydrolysate after 20 hr incubation. G1, G2, G3 and G4 indicate glucose, maltose, maltotriose, and maltotetraose, respectively.
  B. Shows starch hydrolysis time course.

In the preferred method of the invention, the β-amylase is produced by growing a pure culture of *C. thermosulfurogenes* anaerobically on a substrate of starch in a medium containing essential vitamins, minerals and growth factors. The β-amylase is obtained from the culture supernatant substantially free of interfering enzymatic activity.

A detailed description of the preparation and characterization of the enzyme follows:

Materials.

All chemicals used were reagent grade and were obtained from either Mallinckrodt (Paris, Ky., USA) or Sigma Chemical Co. (St. Louis, Mo., USA). Trypticase and yeast extract were obtained from Difco (Detroit, Mich., USA). Hexokinase, glucose-6-phosphate dehydrogenase, *Bacillus* α-amylase, fungal glucoamylase and other biochemicals were obtained from Sigma Chemical Co. (St. Louis, Mo., USA). All gases were obtained from Matheson (Joliet, Ill., USA) and were purified free of oxygen by passage over heated (370° C.) copper filings.

Organism and cultivation.

*C. thermosulfurogenes* strain 4B was isolated from Octopus Spring algal-bacterial mat in Yellowstone National Park (1) and it was deposited in both the Deutsche Sammlung von Mikroorganismen (DSM 2229) and the American Type Culture Collection, Rockville, Md. (ATCC 33743). Stringent anaerobic culture techniques (2) were employed for medium preparation and cultivation. The organism was routinely grown at 60° C. in 26 ml anaerobic pressure tubes (Bellco Glass Co., Vineland, N.J., USA) containing 10 ml of TYE medium (24) with 0.5% glucose or soluble starch and $N_2$-$CO_2$ (95:5) gas headspace. Culture medium was autoclaved for 45 min to ensure destruction of the extremely heat resistant spores of thermoanaerobes (3).

For determination of starch hydrolysis reaction on petri dishes, the organism was streaked in an anaerobic chamber (Coy Products, Ann Arbor, Mich., USA) onto plates of TYE medium that contained 1.0% soluble starch and 3.0% purified agar (Difco). The plates were placed into an anoxic paint can (W. R. Brown Division intermatic, Spring Grove, Ill., USA) under nitrogen and incubated at 60° C. for 4 days, The plates were removed from the paint can and flooded with iodine solution (1% $I_2$, and 2% KI in $H_2O$) and hydrolysis zones were visually observed.

Preparation of enzyme.

Washed cells and culture supernatant as the amylase sources were prepared by cultivating the strain in serum vials that contained 50 ml of TYE medium with 0.5% soluble starch. Stationary phase cultures were then centrifuged at 12,000×g for 10 min. Cell suspensions were prepared by washing twice with 20 mM sodium acetate buffer (pH 6.0) and then suspending the cells in buffer. Large-scale growth for preparation of concentrated extracellular amylase was performed in a 14-liter fermentor (New Brunswick Scientific Co., New Brunswick, N.J., USA) that contained 10 liters of LPBB medium with 1.0% maltose and 0.02% yeast extract under $N_2$-$CO_2$ (95:5). Culture supernatant was obtained from cultures grown at 60° C. until the late exponential phase, using a DuPont (Wilmington) DEO KSB continuous-flow centrifuge system. The supernatant (10 liters) was concentrated first by precipitating proteins with 2 volumes of cold ethanol (20 liters), then filtering through charcoal powder to collect the precipitate, then the precipitate was suspended in 300 ml of 20 mM sodium acetate butter (pH 6.0), and ammonium sulfate was added to 70%. The precipitated proteins were centrifuged at 15,000×g and then suspended in 100 ml of the same buffer as above. This suspension was centrifuged again to remove insoluble materials and then precipitated with 2 volumes of cold acetone. This last precipitate was suspended into 100 ml of the same buffer and, then 100 ml of the enzyme solution was dialyzed against 4 liters of double distilled water for 24 h.

The specific activity of the concentrated supernatant amylase solution was 60 units per mg-protein.

Cells were mass-cultured and harvested for preparation of cell extracts by the same procedures as described above, except TYE medium supplemented with 0.5% soluble starch was employed. Cell extracts were prepared aerobically by suspending 3 g of wet cell paste in 12.5 ml of 20 mM sodium acetate buffer (pH 6.0). This suspension was treated at 37° C. for 1 hr with 5 mg of lysozyme from chicken egg white and disrupted by passage through a French pressure cell at 20,000 lb/in$^2$. The supernatant was collected by centrifugation at 30,000×g for 30 min at 4° C. Protein concentration was determined by the Lowry method.

Enzyme assays.

Amylase or $\beta$-amylase activity was assayed by measurement of reducing sugar released from reaction on starch. The reaction mixtures (1 ml) contained 10% soluble starch, 1 ml of 0.5 M sodium acetate buffer (pH 6.0); and 3 ml enzyme solution which was appropriately diluted with water. The reaction was stopped by cooling on ice after 30 min incubation at 60° C.

Reducing power was measured by the dinitrosalicylic acid method. For assay of pullulanase activity, the reaction mixture consisted of 0.5 ml of 2% pullulan in 0.2 M sodium acetate buffer (pH 6.0) and 0.5 ml enzyme solution. After incubation at 60° C. for 30 min, the reaction was stopped by cooling on ice and by adding 4 ml of 3,5-dinitrosalicylic acid.

One unit of amylase, $\beta$-amylase or pullulanase is defined as the amount of enzyme that produced 1 $\mu$mol of reducing sugar as a glucose standard per min under the above conditions.

Glucoamylase activity was assayed by incubating 1 ml of reaction mixture that contained 1% soluble starch, 0.1 M sodium acetate buffer (pH 4.8) and the appropriately diluted enzyme solution at 60° C. for 30 min. The reaction was stopped immediately by cooling on ice and then by boiling in a steam bath for 10 min. These reaction mixtures were centrifuged to remove the insoluble precipitates, and then released glucose was analyzed by the hexokinase and glucose-6-phosphate dehydrogenase method. A unit of glucoamylase is defined as the amount of enzyme that produced one $\mu$mol of glucose per min under the assay conditions.

Qualitative and quantitative analysis of starch hydrolysis products.

Enzyme (12 units) was placed into 20 ml of 0.1 M sodium acetate butter (pH 6) containing 1% soluble starch and incubated at 65° C. Samples were withdrawn at intervals and reducing sugar and glucose content were analyzed as described above, Maltose was identified in the starch hydrolysates by high pressure liquid chromatography (HPLC). The separation system consisted of a Perkin-Elmer series B liquid chromatograph equipped with a Sigma 10 data station (Perkin Elmer Corp., Norwalk, Conn., USA), a refractive index detector (Laboratory Data Control, Riviera Beach, Fla., USA) and a Biorad oligosaccharide Analysis Column (300×7.8 mm, Aminex HPX-42A) fitted with a microguard pre-column (40×4.6 mm packed with Aminex HPX-85C) (Biorad Laboratories, Richmond, Calif., USA). Starch hydrolysate samples were centrifuged at 5,000×g and loaded onto the column (50 1).

Determination of reducing value and blue value curve.

A reaction mixture used enzyme and a 0.25% amylose solution in 0.1 M sodium acetate buffer (pH 6.0) and were incubated at 65° C. Samples (0.5 ml) were withdrawn at 5 min intervals and were placed in tubes that contained 2 ml of 0.1 M HCl for determination of blue value. After mixing, 0.5 ml samples were withdrawn and added to 5 ml of iodine solution (0.05 g of iodine and 0.5 g of potassium iodide per liter). Then, absorbance was measured at 620 nm in a spectrophotometer blanked against water-iodine. The blue value was calculated by dividing the absorbance of the digest with that of the substrate-iodine blank and multiplying by 100. Another 0.5 ml sample of the reaction mixture was withdrawn for determinations of reducing value. The reducing power was analyzed by the Nelson colorimetric copper method. Total carbohydrate was assayed by the phenol-sulfuric acid method.

Optical rotation study.

A reaction mixture (5 ml) consisting of 1% starch solution in 0.1 M sodium acetate buffer (pH 6.0) and enzyme was added to a 10 cm cell. Optical rotation was measured at room temperature in a Perkin Elmer Model 214 polarimeter using the sodium line. When the optimal rotation became approximately constant, about 20 mg of solid sodium carbonate was added and the mutarotation of the mixture was measured.

Enzyme characterization.

The enzyme inhibition and kinetic studies were performed under the standard assay conditions described above. The stability studies employed enzyme solution (about 40 units/ml) in 0.1 M sodium acetate buffer (pH 6.0) under the described conditions.

Location and type of amylase activities.

In preliminary experiments, large reddish color zones against a blue background were detected around colonies on starch agar plates that were stained with iodine solution. This result implied the *C. thermosulfurogenes* produces amylases that are not capable of completely hydrolyzing starch.

Table 1 summarizes the results of experiments demonstrating the cellular location and types of different amylase activities in *C. thermosulfurogenes*. The organism produced extracellular amylase, whose activity will be classifed below as β-amylase, but not extracellular pullulanase or glucoamylase during growth. In addition, cell bound glucoamylase and amylase but not pullulanase activity was detected. Neither amylase nor glucoamylase activities were inhibited by aerobic assay conditions.

TABLE 1

Amylolytic Enzyme Activities and Cellular Location in *C. thermosulfurogenes*[a]

| Enzyme | Assay Condition | Location - Activity Supernatant (U/ml) | Washed Cells (U/ml) | Cell-Free Extracts (U/mg Protein) |
|---|---|---|---|---|
| Amylase | Aerobic | 5.5 | 0.07 | 0.26 |
|  | Anaerobic | 5.5 | 0.07 | 0.26 |
| Pullulanase | Aerobic | 0.00 | 0.00 | 0.00 |
|  | Anaerobic | 0.00 | 0.00 | 0.00 |
| Glucoamylase | Aerobic | 0.00 | 0.02 | 0.07 |
|  | Anaerobic | 0.00 | 0.02 | 0.07 |

[a]*C. thermosulfurogenes* was grown to the late exponential phase on TYE medium that contained 0.5% soluble starch as carbon source. Anaerobic assay conditions were established via addition of dithiothreitol (2 mM) and gassing with $N_2$ gas in preparation of enzyme solution and all reactants.

Figure 1B:
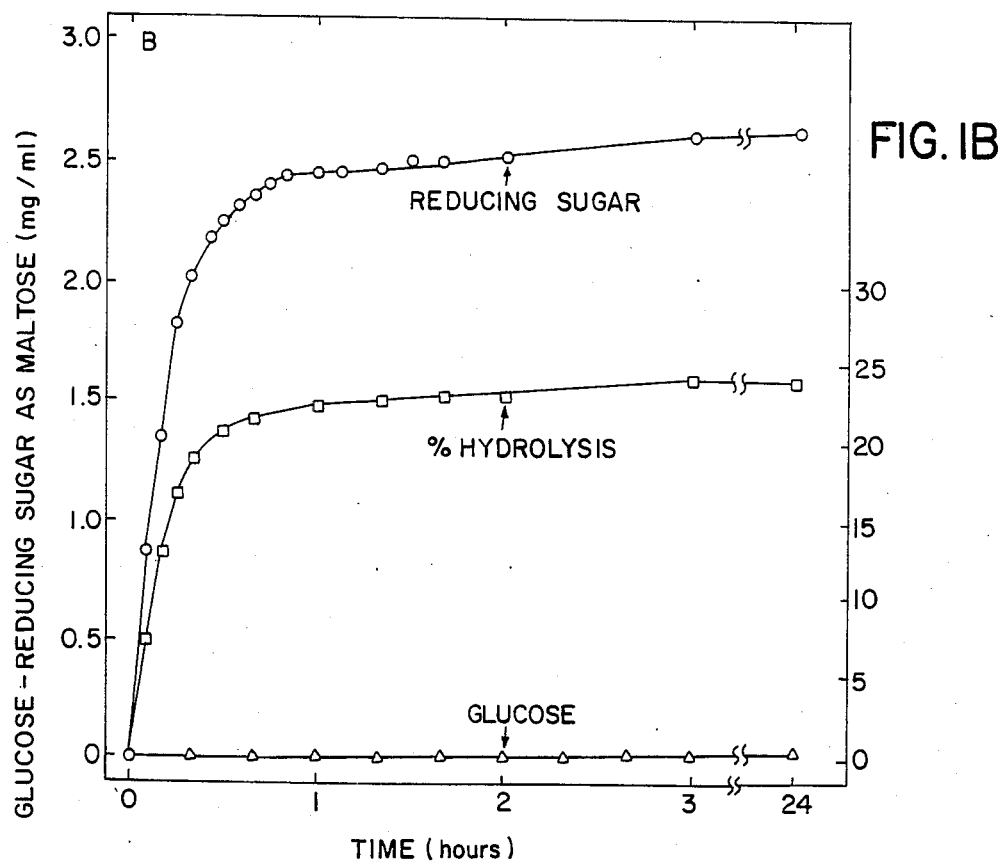

HPLC analysis of starch hydrolysates formed by extracellular amylase (FIG. 1A) revealed that only maltose was produced as a detectable product in addition to high molecular weight oligosaccharides (i.e., limit-dextrins). In spite of prolonged incubation (FIG. 1B), only reducing sugars but not glucose were detected by quantatitive analysis of starch hydrolysates. Enzymatic hydrolysis of maltotriose and maltotetraose hydrolysis were also studied. Only maltose (8 mg/ml was) produced as a result of incubating 1% maltotetraose in 0.1 M sodium acetate buffer with 12 units of the enzyme at 65° C. for 3 hrs. Under these same conditions, enzymatic hydrolysis of maltotriose (1%) yielded both glucose (0.4 mg/ml) and maltose.

Figure 2:
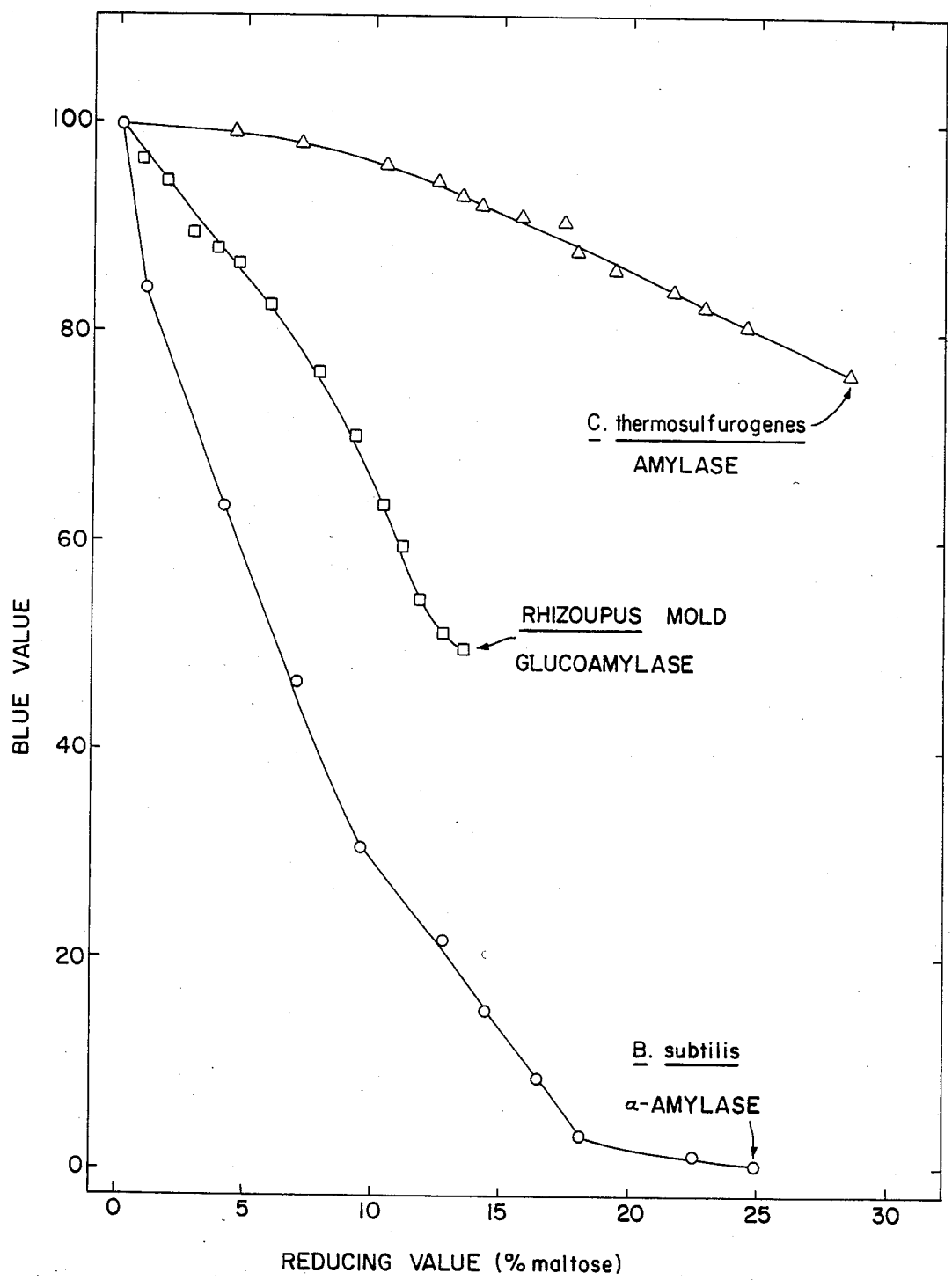
FIG. 2. Shows the reducing value curves on amylose for *C. thermosulfurogenes* extracellular amylase, *Rhizopus* mold glucoamylase and *Bacillus subtilis* α-amylase. The reaction was performed in serum vials that contained 20 ml of 0.25% amylose in 0.1 M acetate buffer (pH 6.0), the respective enzyme (3 units each), and at 65° C. for *C. thermosulfurogenes* amylase but at 50° C. for others.
Figure 3:
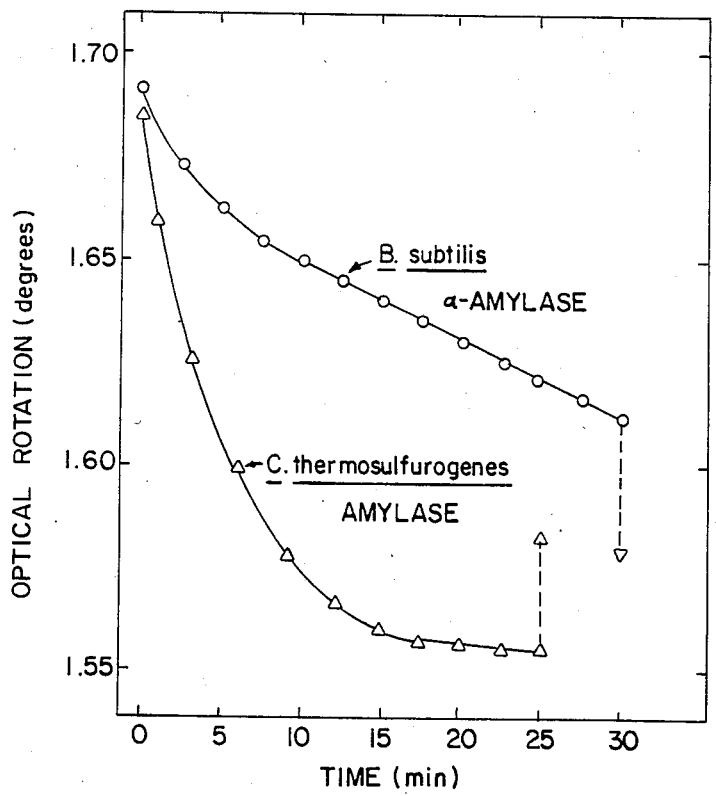
FIG. 3. Shows the results of an optical rotation study on the action of *C. thermosulfurogenes* extracellular amylase and *B. subtilis* α-amylase with starch. The arrows indicate the optical rotation after addition of sodium carbonate to the digests.

FIG. 2 shows the release of reducing power and reduction of iodine staining capacity by action of the enzyme on amylose. The slow decrease of blue value against reducing value in comparison with that of the α-amylase control indicates that the enzyme is an exo-acting amylase. From the mutarotation study (FIG. 3), which employed α-amylase as control, the upward shift of optical rotation upon the addition of base to the starch hydrolysate formed by the *C. thermosulfurogenes* enzyme indicates that the hydrolysis products have a β-anomeric configuration. The data above provided evidence that the extracellular amylase activity isolated from *C. thermosulfurogenes* was a β-amylase.

Physicochemical properties of β-amylase.

Figure 4A:
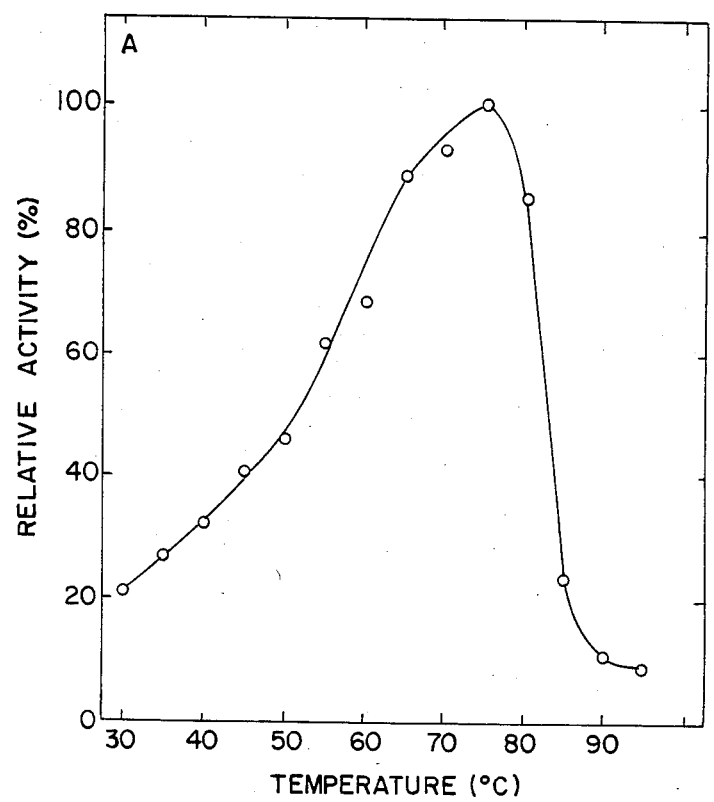
FIG. 4. Shows the effects of temperature on activity and stability of *C. thermosulfurogenes* β-amylase in the presence (A and B) or absence (C) of starch.
  A. Shows the temperature profile of the β-amylase activity. 100% activity corresponds to 57 units/mg-protein.
  B. Shows the thermal stability of β-amylase. The enzyme solutions (0.31 mg-protein/ml) in 0.1 M acetate buffer (pH 6.0) were incubated at the stated temperature. The residual activity was assayed under the standard conditions, and 100% activity corresponds to 24.4 units/mg-protein.
  C. Shows the effects of starch on thermal stability of β-amylase, Experiments were performed as in B, except for the addition of indicated starch.

The effect of temperature on the activity of β-amylase is illustrated in FIG. 4A. The optimum temperature for the enzyme activity was 75° C., and 85% of maximal activity was measured at 80° C. When Arhennious plots of specific activity versus 1/temperatures were determined (data not shown), $Q_{10}$, values of 1.7 were calculated for β-amylase.

Figure 4B:
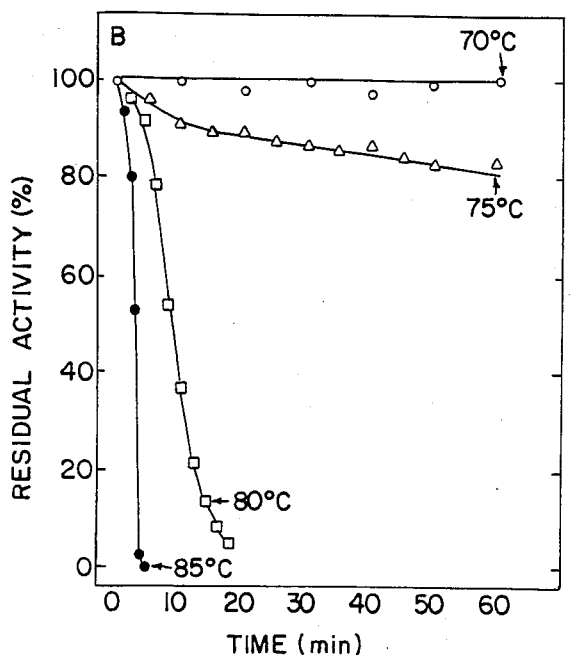
Figure 4D:
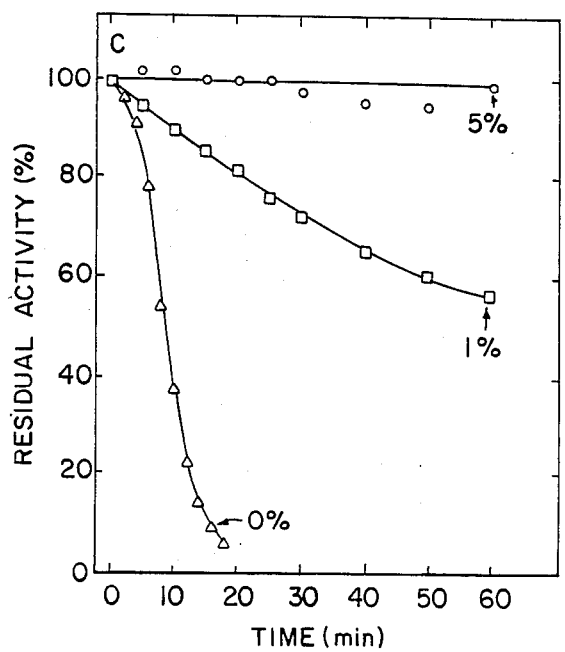

The effect of temperature on the stability of the β-amylase in the absence of substrate is shown in FIG. 4B. The enzyme was completely stable up to 70° C. and 83% of the original activity was retained after treatment at 75° C. for 1 hr. FIG. 4C shows that the enzyme was almost completely destroyed within 20 min at 80° C. in the absence of starch, but addition of starch to the enzyme solution greatly enhanced the heat-stability in proportion to the concentration of starch. The enzyme was entirely stable at 80° C. in the presence of 5% starch.

Figure 5A:
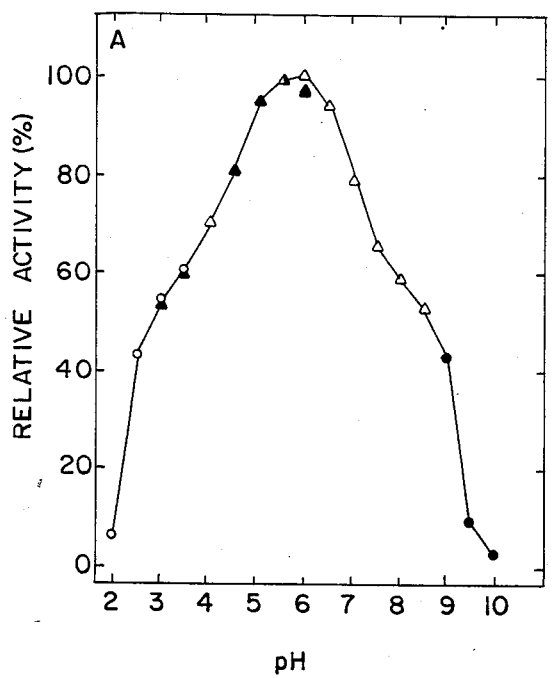
FIG. 5. Shows the dependence of *C. thermosulfurogenes* β-amylase activity and stability on pH. 100% activity corresponds to 24.4 units/mg-protein.
  A. Shows the pH dependence of enzyme activity. Enzyme activities were assayed using 50 mM glycine-HCl (—o—), sodium acetate (—▲—), sodium phosphage (—Δ—), and glycine-Na buffer (—●—)
  B. Shows the pH stability of the enzyme. The enzyme solutions (0.62 mg-protein/ml) in the same buffers as above, were incubated at 60° C. for 1 hr. and the residual activites were assayed under the standard conditions.
Figure 5B:
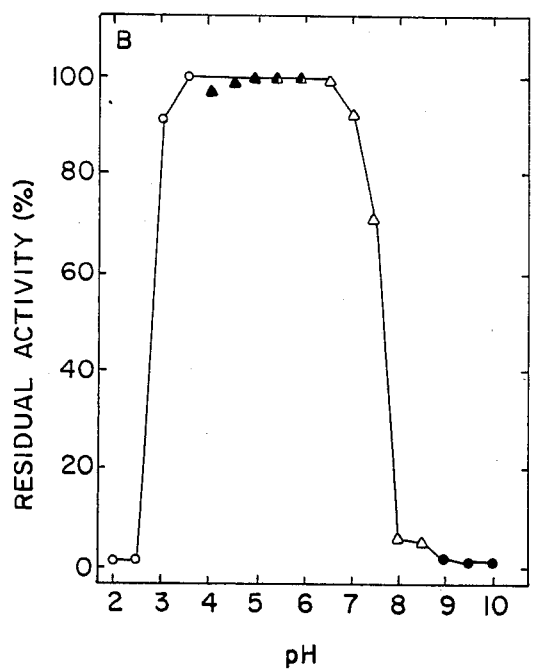

FIG. 5 shows the effect of pH on β-amylase activity and stability. The optimum activity was observed at pH 5.5 to 6.0, and the activity dropped gradually at more alkaline or acid pH values. Higher than 43% of maximal activity was detected between pH values of 2.5 and 9.0. The enzyme was stable in the pH range of 3.5 to 6.5, but unstable below pH 3.0 and above pH 7.5.

The effects of sulfhydryl reagents, metal ions and Schardinger dextrins (α and β-cyclodextrin) on β-amylase activity were examined and are reported in Table 2. β-Amylase activity was strongly inhibited by $CU^{++}$, $Hg^{++}$ and p-chloromercuribenzoate (PCMB), but weakly inhibited by hydrogen peroxide, 5,5'- dithiobis-2-nitrobenzoic acid, N-ethylmaleimide (NEM), iodocetic acid and $Zn^{++}$. The inhibitions could be prevented and restored by the addition of dithiothreitol (10 mM). The Schardinger dextrins, unexpectedly, did not inhibit enzyme activity and were not hydrolyzed by the β-amylase. Under the assay condition used, the enzyme activity was not affected by the addition of 1 to 30 mM of calcium ion.

TABLE 2

Effects of Sulfhydryl Reagents, Metal Ions and Schardinger Dextrins on β-Amylase Activity

| Concentration of Reagent Added (mM) | % Activity[a] Remaining |
|---|---|
| None | 100 |
| Hydrogen peroxidase - 1 | 98 |
| 5 | 86 |
| 5,5'-dithiobis-2-nitrobenzoic acid (DTNB) - 0.2 | 96 |
| N—ethylmaleimide (NEM) - 1 | 93 |
| 5 | 54 |
| Iodocaetate (IA) - 1 | 100 |
| 5 | 52 |

TABLE 2-continued

Effects of Sulfhydryl Reagents, Metal Ions and Schardinger Dextrins on β-Amylase Activity

| Concentration of Reagent Added (mM) | % Activity[a] Remaining |
|---|---|
| p-chloromercuribenzoic acid - 0.02 | 0.2 |
| (pCMB) - 0.1 | 0.0 |
| CuCl$_2$ - 1 | 1.8 |
| HgCl$_2$ - 1 | 0.0 |
| ZnCl$_2$ - 1 | 93 |
| - 10 | 73 |
| CaCl$_2$ - 5 | 100 |
| - 30 | 100 |
| α-Cylcodextrin - 10 | 100 |
| β-Cyclodextrin - 10 | 100 |

[a]100% activity corresponds to 24.4 units/mg protein under the standard assay conditions.

The effects of ethanol on the enzyme activity and stability were also performed, β-Amylase activity was not notably affected in the presence of 3% (v/v) ethanol, but it dropped slowly in proportion to the concentration of ethanol at higher than 3% (v/v). In the presence of 10% (v/v) ethanol, 65% of maximal activity was observed. This effect is attributed to the precipitation of starch substrate by ethanol because β-amalyse was completely stable at 65° C. for 1 hr in presence of 10% (v/v) ethanol prior to activity analysis.

Kinetic properties of β-amylase.

Figure 6:
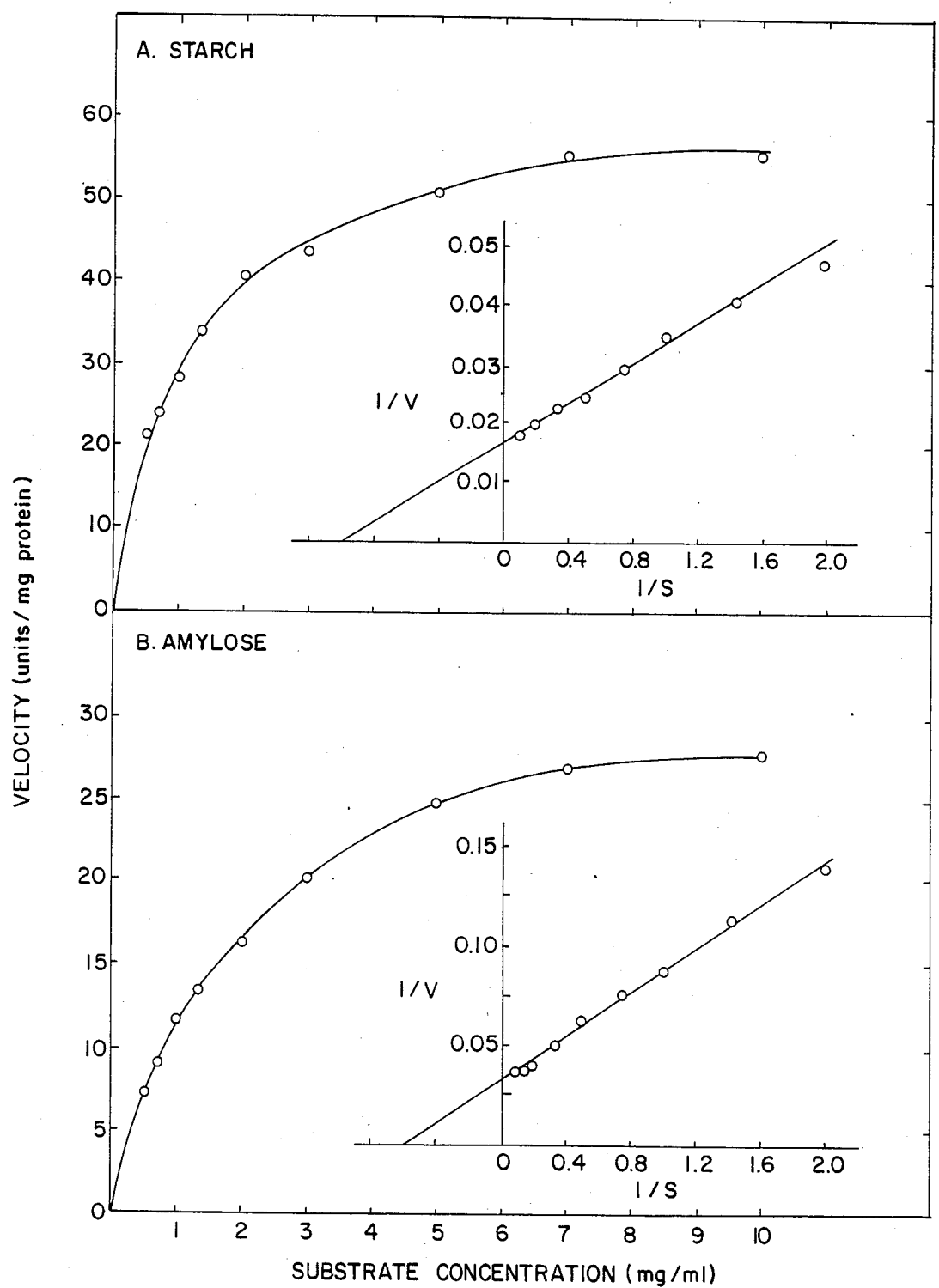
FIG. 6. Shows the kinetic properties of *C. thermosulfurogenes* β-amylase on starch versus amylose. Reaction mixtures contained 0.1 M acetate buffer (pH 6.0), β-amylase (9.4 μg/ml), and the appropriate amounts of substrates. During incubation at 65° C., the samples were withdrawn at intervals for measurement of initial reaction rates.

The apparent kinetic constants were determined for β-amylase on starch versus amylose by determination of production formation rate versus time curves. FIG. 6 demonstrates that the dependence of the rate of enzymatic hydrolysis on the substrate concentration followed Michaelis-Menten kinetics and that linear relationships of 1/V versus 1/[S] were obtained. The apparent $[S]_{0.5V}$ and Vmax as determined from the double reciprocal for starch versus amylose were: 1 mg/ml and 60 U/mg protein verus 1.67 mg/ml and 30 U/mg protein, respectively.

In general, the foregoing data establish that *C. thermosulfurogenes* produces both cell bound glucoamylase and extracellular β-amylase activities. The β-amylase is produced in high yield as a primary metabolite during growth on starch. The β-amylase possessed a high thermal stability which may make it of industrial utility in brewing and starch processing.

The extracellular amylase was classifed as a β-amylase based on certain criteria (4,5,6,7). The action of the enzyme on starch yielded only maltose as a detectable product besides high molecular weight limit dextrin, but not glucose or other low molecular maltosaccharides. Maltotetraose hydrolysis yielded only maltose, and maltotriose yielded glucose and maltose. The enzyme was inactive against pullulan, sucrose, cellobiose, trehalose, Schardinger dextrins and maltose. A large release of reducing power with relatively little reduction of the iodine-staining capacity on hydrolysis of amylose and the upward mutarotation of starch digest upon the addition of alkali indicated that the enzyme acts in an exo-fashion and produced maltose with the β-anomeric configuration. In these respects, the extracellular amylase of *C. thermosulfurogenes* was similar in the action patterns of plant and other microbial β-amylases.

The β-amylase has industrial applications in the production of various sugar solutions or alcohols from starch because of its novel features. The enzyme is extracellular, a primary metabolite and it is active and stable at high temperature. The enzyme displays a high maximum temperature (75° C.) for enzyme activity and is stable up to 80° C. in the presence of substrate. The β-amylase is also active and stable at a wide range of pH. It has an optimal activity (pH 5.5–6.0), and stability (pH 3.5–6.5) in the acidic range, which distinguishes it from most other β-amylases that display optimal activity and stability around a neutral pH. The β-amylase also may have novel applications for production of maltose syrups in conjunction with a pullulanase which is active at nearly the same pH and temperature range.

β-Amylases from higher plant and microorganisms are sulfhydryl enzymes and are inactivated by sulfhydryl reagents or oxidation. The present data indicates that *C. thermosulfurogenes* β-amylase is also inactivated by sulfhydryl reagents (i.e., PCMB, NEM). However, this inhibition could be prevented and reversed by the addition of reducing agent (dithiothreitol). Also, metal ions (e.g., Cu++, Hg=++ and Fe++) inhibited the β-amylase. However, Schardinger dextrins which notably are competitive inhibitors of other β-amylases (5, 6), did not inhibit the β-amylase of *C. thermosulfurogenes*.

The β-amylase activity and stability was little affected by ethanol although growth of this species was very sensitive (i.e., no growth in the presence of 2% ethanol).

REFERENCES

1. Schink, B., and J. G. Zeikus. 1983. *Clostridium thermosulfurogenes* sp. nov., a new thermophile that produces elemental sulphur from thiosulphate. J. Gen. Microbiol. 129; 1149–1158.
2. Zekus, J. G., A. Ben-Bassat, and P. Hegge. 1980. Microbiology of methanogensis in thermal, volcanic environments. J. Bact. 143: 432–440.
3. Hyun, H. H., J. G. Zeikus, R. Longin, J. Millet, and A. Ryter. 1983. Ultrastructure and extreme heat resistance of spores from thermophilic Clostridia. J. Bact. 156: 1332–1337.
4. Fogarty, W. M., and C. T. Kelly. 1979. Starch-degrading enzymes of microbial origin. Prog. Ind. Microbiol. 15: 87–150.
5. Fogarty, W. M., and C. T. Kelly, 1980. Amylases, amyloglucosidases and related glucanases, p. 115–169. In A. H. Rose (ed.), Microbial enzymes and bioconversions, Academic Press Inc., New York.
6. Robyt, J. F., and W. J. Whelan. 1968. The β-amylases, p. 477–497. In J. A. Radley (ed.), Starch and Its Derivatives, Chapman and Hall Ltd.
7. Thomas, M. F., F. G. Priest, and J. R. Stark. 1980. Characterization of an extracellular β-amylase from *Bacillus megaterium sensu stricto*. J. Gen. Microbiol. 118: 67–72.
8. Schink, B., and J. G. Zeikus. 1983. Characterization of pectinolytic enzymes of *Clostridium thermosulfurogenes*. FEMS Microb. Letters 17: 295–298.

It had previously been discovered that *C. thermosulfurogenes* produced pectinolytic enzymes (8) but is was not known that it produced an extracellular thermostable β-amylase.

It will be appreciated by those skilled in the art that βamylase productivity may be enhanced through mutation of the organism or by genetic recombination techniques. Therefore, the scope of the invention should not be limited to the specific strain of the organism described above because any organism capable of producing a thermostable β-amylase similar to that produced by *C. thermosulfurogenes* having the identifying characteristics of ATCC 33743 can be used.

We claim:

1. A thermostable β-amylase, substantially free of interfering saccharidase enzymatic activity from the microorganism *Clostridium thermosulfurogenes*, said β-amylase having an optimum temperature for activity of about 75° C.; said β-amylase being stable up to 70° C. in the absence of substrate and up to 80° C. in the presence of substrate; said enzyme having optimum activity at about pH 5.5 to about 6.0 and being stable from about pH 3.5 to about 6.5.

2. A thermostable β-amylase from *Clostridium thermosulfurogenes*, said β-amylase having the following physiochemical properties:

(1) Reactivity: It produces only maltose and limited dextrins when transforming starch hydrolysates;

(2) Substrate specificity: It produces only maltose from starch or maltotetraose and glucose and maltose from maltotriose;

(3) Optimum pH value: About 5.5 to about 6.0;

(4) pH stability: Stable from about pH 3.5 to about 6.5;

(5) Optimum temperature: 75° C., 85% of maximal activity at 80° C.;

(6) Temperature stability: It is stable up to 70° C. in the absence of substrate and up to 80° C. in the presence of 5% starch; and (7) Influence of inhibitors: β-amylase activity inhibited by metal ions ($Cu^{++}$ and $Hg^{++}$) and p-chloromercuribenzoate but not by calcium Schandingder dextrins or ethanol.

3. A method for producing a thermostable, β-amylase which comprise anaerobically culturing a β-amylase producing *Clostridium thermosulfurogenes* in a nutrient medium until substantial enzymatic activity is detectable and thereafter isolating the thermostable β-amylase.

* * * * *